United States Patent
Booker et al.

(10) Patent No.: US 9,989,466 B2
(45) Date of Patent: Jun. 5, 2018

(54) METHOD FOR REDUCING ANALYZER VARIABILITY USING A NORMALIZATION TARGET

(71) Applicant: Quidel Corporation, San Diego, CA (US)

(72) Inventors: David Dickson Booker, Albuquerque, NM (US); Jhobe Steadman, Poway, CA (US)

(73) Assignee: Quidel Corporation, San Diego, CA (US)

( * ) Notice: Subject to any disclaimer, the term of this patent is extended or adjusted under 35 U.S.C. 154(b) by 614 days.

(21) Appl. No.: 14/562,060

(22) Filed: Dec. 5, 2014

(65) Prior Publication Data

US 2015/0160134 A1   Jun. 11, 2015

Related U.S. Application Data

(60) Provisional application No. 61/913,078, filed on Dec. 6, 2013.

(51) Int. Cl.
| | | |
|---|---|---|
| *G01N 21/27* | (2006.01) | |
| *G01N 21/64* | (2006.01) | |
| *G01N 33/543* | (2006.01) | |

(52) U.S. Cl.
CPC ......... *G01N 21/645* (2013.01); *G01N 21/274* (2013.01); *G01N 21/278* (2013.01); *G01N 33/54386* (2013.01); *G01N 2201/062* (2013.01); *G01N 2201/068* (2013.01); *G01N 2201/10* (2013.01); *G01N 2201/12746* (2013.01); *G01N 2201/12753* (2013.01); *G01N 2201/12761* (2013.01)

(58) Field of Classification Search
CPC ..... G01N 2201/06; G01N 2201/12746; G01N 2201/13
See application file for complete search history.

(56) References Cited

U.S. PATENT DOCUMENTS

| | | |
|---|---|---|
| 4,934,817 A | 6/1990 | Gassenhuber |
| 5,204,264 A | 4/1993 | Kaminer et al. |
| 5,238,737 A | 8/1993 | Burkhardt et al. |
| 5,414,258 A | 5/1995 | Liana |
| 5,766,961 A | 6/1998 | Pawlak |

(Continued)

FOREIGN PATENT DOCUMENTS

| | | |
|---|---|---|
| EP | 0174722 A2 | 3/1986 |
| JP | 2003-083970 A | 3/2003 |

(Continued)

OTHER PUBLICATIONS

Giebeler et al., "Performance validation for microplate fiuorimeters", vol. 15, No. 3. pp. 363-375 (2005).

(Continued)

*Primary Examiner* — Cheung Lee
(74) *Attorney, Agent, or Firm* — McDermott Will & Emery LLP

(57) ABSTRACT

Disclosed herein is a method for improving the precision of a test result from an instrument with an optical system that detects a signal. The method comprises including in the instrument a normalization target disposed directly or indirectly in the optical path of the optical system. Also disclosed are instruments comprising a normalization target, and systems comprising such an instrument and a test device that receives a sample suspected of containing an analyte.

19 Claims, 6 Drawing Sheets

(56) References Cited

U.S. PATENT DOCUMENTS

| | | | |
|---|---|---|---|
| 5,770,460 | A | 6/1998 | Pawlak et al. |
| 6,074,616 | A | 6/2000 | Buechler et al. |
| 6,136,610 | A | 10/2000 | Polito et al. |
| 6,144,455 | A | 11/2000 | Tuunanen et al. |
| 6,267,722 | B1 | 7/2001 | Anderson et al. |
| 6,392,894 | B1 | 5/2002 | Buechler et al. |
| 6,394,952 | B1 | 5/2002 | Anderson et al. |
| 6,727,073 | B1 | 4/2004 | Moore et al. |
| 6,830,731 | B1 | 12/2004 | Buechler et al. |
| 6,867,051 | B1 | 3/2005 | Anderson et al. |
| 6,878,947 | B2 | 4/2005 | Haberstroh |
| 6,936,476 | B1 | 8/2005 | Anderson et al. |
| 7,002,688 | B2 | 2/2006 | Aravanis et al. |
| 7,437,913 | B2 | 10/2008 | Djennati et al. |
| 7,521,249 | B2 | 4/2009 | Rosen et al. |
| 7,521,260 | B2 | 4/2009 | Petruno et al. |
| D606,664 | S | 12/2009 | Jacono et al. |
| 7,632,687 | B2 | 12/2009 | Gokhan |
| 7,784,679 | B2 | 8/2010 | Kuo et al. |
| 7,925,445 | B2 | 4/2011 | Petrilla et al. |
| 8,039,783 | B2 | 10/2011 | Lai |
| 8,043,867 | B2 | 10/2011 | Petruno et al. |
| 8,128,871 | B2 | 3/2012 | Petruno et al. |
| 8,334,522 | B2 | 12/2012 | Egger |
| 2002/0190356 | A1 | 12/2002 | Buechler et al. |
| 2004/0018637 | A1 | 1/2004 | Polito et al. |
| 2004/0241047 | A1 | 12/2004 | Buechler et al. |
| 2005/0017076 | A1 | 1/2005 | Hosokawa et al. |
| 2006/0228554 | A1 | 10/2006 | Tan et al. |
| 2007/0154970 | A1 | 7/2007 | Buechler et al. |
| 2007/0236692 | A1 | 10/2007 | Schebesta et al. |
| 2008/0031779 | A1 | 2/2008 | Polito et al. |
| 2008/0081341 | A1 | 4/2008 | Maher et al. |
| 2008/0199851 | A1 | 8/2008 | Egan et al. |
| 2008/0311002 | A1 | 12/2008 | Kirby et al. |
| 2009/0061507 | A1 | 3/2009 | Ho |
| 2009/0142856 | A1 | 6/2009 | Hudak et al. |
| 2009/0263854 | A1 | 10/2009 | Jacono et al. |
| 2010/0068826 | A1 | 3/2010 | Gokhan |
| 2010/0117003 | A1 | 5/2010 | Egger |
| 2010/0135857 | A1 | 6/2010 | Hunter et al. |
| 2010/0311181 | A1 | 12/2010 | Abraham et al. |
| 2011/0043618 | A1 | 2/2011 | Salisbury et al. |
| 2012/0021531 | A1 | 1/2012 | Ellis et al. |
| 2012/0071342 | A1 | 3/2012 | Lochhead et al. |
| 2012/0223251 | A1 | 9/2012 | Morrow et al. |
| 2012/0300205 | A1 | 11/2012 | Misener et al. |
| 2013/0230844 | A1 | 9/2013 | Egan et al. |
| 2013/0230845 | A1 | 9/2013 | Egan et al. |

FOREIGN PATENT DOCUMENTS

| | | |
|---|---|---|
| WO | WO 1999/039298 A1 | 8/1999 |
| WO | WO 2000/031539 A1 | 6/2000 |
| WO | WO 2005/031355 A1 | 4/2005 |
| WO | WO 2009/014787 A2 | 1/2009 |
| WO | WO 2013/131052 A1 | 9/2013 |
| WO | WO 2013/131057 A1 | 9/2013 |

OTHER PUBLICATIONS

International Search Report from PCT Patent Application No. PCT/US2014/068829 dated Mar. 6, 2015.

Egan et al., "High sensitivity immunofluorescence influenza A+B assay with reader", 27th Annual Clinical Virology Symposium, May 8-11, 2011, 1 page (2011) *Abstract*.

International Search Report from PCT Patent Application No. PCT/US2013/028743 dated May 28, 2013, application now published as PCT Publication No. WO2013/131052 dated Sep. 6, 2013.

International Search Report from PCT Patent Application No. PCT/US2013/028749 dated Jul. 1, 2013, application now published as PCT Publication No. WO2013/131057 dated Sep. 6, 2013.

Van Dyke et al., "Multiplex point of care (POC) assay for the detection community acquired resoiratory viruses", 27th Annual Clinical Virology Symposium, Poster, May 8-11, 2011, 2 pages (2011) *Abstract*.

METHOD FOR REDUCING ANALYZER VARIABILITY USING A NORMALIZATION TARGET

CROSS-REFERENCE TO RELATED APPLICATIONS

This application claims the benefit of U.S. Provisional Application No. 61/913,078, filed Dec. 6, 2013, incorporated herein by reference in its entirety.

TECHNICAL FIELD

The subject matter described herein relates to systems, methods and apparatuses for improving the precision and reducing variability of an optical analyzer, used in sample analysis to aid in medical diagnosis or detection of the presence or absence of an analyte in the sample.

BACKGROUND

Assay devices, including detection gels, microfluidic devices, immunoassays, and the like, for detection of an analyte in a sample are known in the art. In particular, lateral flow immunoassay devices are routinely used for detecting the presence of an analyte in a sample. Lateral flow immunoassay devices often use a labeled specific-binding reagent that is releasably immobilized on a test strip of porous material. A liquid sample, such as a biological sample from a human or an environmental sample, is applied to an end of the porous strip and the capillary properties of the strip transports the liquid sample along the strip, releasing the labeled specific binding reagent, which binds specifically to the analyte of interest at a first binding site thereof, if present, in the sample. The labeled binding reagent is then typically captured at a test zone by a second reagent having specific binding for a second binding site of the analyte of interest. Excess labeled binding reagent is captured at a control zone, downstream of the test zone by a control reagent which binds specifically to the labeled reagent.

Commercially available lateral flow assay devices are typically designed to be read by the naked eye of the user or to be read by an instrument. An instrument designed to read a signal emanating from a lateral flow device offers superior sensitivity relative to visually (i.e., naked eye) read devices, as the optical system in an apparatus is able to detect intensities and wavelengths not visible to the naked eye.

A concern with instruments for reading lateral flow devices is the lack of precision, due to inter-instrument and/or operator variability. There remains a need in the art for an apparatus and a system that objectively analyses a signal from an immunoassay test device, where the apparatus has improved sensitivity, accuracy and/or precision for determining the presence or amount of signal from a lateral flow device.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated hereinbelow are meant to be exemplary and illustrative, not limiting in scope.

In some aspects, an apparatus for detection of a signal from a test device indicative of the presence or absence of an analyte in a sample is provided.

In some aspects, a method to improve precision, accuracy or both of a test result from an optical instrument previously calibrated with an external calibrant is provided. The method comprises (a) assigning a normalization value to a normalization target embedded in or on the instrument, the normalization value being assigned with respect to the previous calibration, and storing the normalization value in instrument memory; (b) interrogating: (i) a test cartridge inserted into the instrument to obtain a test signal; and (ii) the embedded normalization target to obtain a current value each (the test cartridge and its target, as well as the embedded normalization target); and (c) optionally adjusting the test signal by a scaling factor, thereby obtaining a scaled test result.

In one embodiment, assigning a normalization value to the normalization target comprises optically scanning the normalization target to obtain a signal from the normalization target or interrogating the normalization target to obtain light output data. In one embodiment, optically scanning or interrogating the normalization target is conducted in a single, continuous optical scan (or single data collection event) of the normalization target and the external calibrant.

In one embodiment, assigning a normalization value to the normalization target comprises optically gathering signal data by imaging the calibrant and the normalization target in a single image to obtain a signal from the normalization target and the calibrant. In one embodiment, the imaging system of the instrument obtains location dependent light emission data from the test device and the normalization target in a single data collection event.

In one embodiment, step (b) scanning comprises scanning in a single, continuous scan; that is, where the optical system initiates a pass along its optical pathway continuously and/or mechanically uninterrupted. That is, the imaging system of the instrument obtains location dependent light emission data from the test device and the normalization target in a single data collection event. Scanning, in one embodiment, contemplates securing an image using, for example, a CCD or a CMOS optical light gathering chips to image the test strip and the normalization target in a single event.

In some aspects, a method to improve precision, accuracy or both of a test signal from an optical instrument is provided. The method can comprise (a) providing an instrument pre-calibrated with an external calibrant, wherein the instrument comprises an embedded normalization target; (b) collecting light emission data and assigning a normalization value to the embedded normalization target, wherein the normalization value is assigned with respect to the previous calibration, and wherein the normalization value is stored in instrument memory; (c) interrogating: (i) a test cartridge inserted into the instrument to obtain a test signal; and (ii) the embedded normalization target to obtain a current value; and (d) optionally adjusting the test signal by a scaling factor, thereby obtaining a scaled test result with improved precision relative to the unadjusted test signal.

In one embodiment, step (c) interrogating comprises scanning or imaging in a single data collection event (e.g., a continuous scan where an optical system initiates a pass along its optical pathway continuously and/or mechanically uninterrupted.)

In some aspects, a method and a system are provided for quantatitive or qualitative measurement of an analyte in a test sample. The system may comprise an instrument with an optical pathway comprising (i) an optics module or a fixed digital camera capable of interrogating a test strip comprising the test sample when the test strip is positioned in the optical pathway and (ii) an embedded normalization target affixed to the instrument directly or indirectly in the optical pathway; and an external calibrant insertable into the instrument, directly or indirectly in the optical pathway.

In some embodiments, the test cartridge is scanned or interrogated concurrently with the embedded normalization target. In some embodiments, the test cartridge is scanned or interrogated subsequent to the embedded normalization target.

In some embodiments, if the normalization value exceeds a predefined value, a communication to a user is generated by the instrument. In some embodiments, if the assigned normalization value differs from the current value by more than x %, the instrument issues a communication to the user. In some embodiments, the communication advises that the instrument requires re-calibration and/or normalization with the embedded normalization target. In some embodiments, the communication advises that an updated normalization value should be assigned to the embedded normalization target. In some embodiments, the value of x is about 0.5%, 1%, 1.5%, 2%, 3%, 4%, 5%, 6%, 7%, 8%, 9%, 10%, 12%, 14%, 15%, 18% or 20%.

In some embodiments, collecting light emission data comprises interrogating (or optically scanning) with an excitation wavelength between about 300-800 nm, or between about 320-780 nm, or between about 340-750 nm, or between about 340-800 nm, or between about 300-700 nm. In other embodiments, the instrument comprises filters that cut off wavelengths less than about 300 nm and greater than about 500 nm so the test device is not exposed to wavelengths that are below or above these wavelengths.

In some embodiments, the scaling factor used to adjust the test signal is a ratio of the current value to the assigned normalization value. In some embodiments, the instrument does not adjust the test signal by the scaling factor. In some embodiments, the calculation of the scaled value of the test signal may be represented by the equation: $ENT_{obs}/ENT_{NV}$·test value=scaled value, where "ENT" represents the embedded normalization target, "obs" intends observed (the empirical value); and "NV" denotes normalization value.

In order to prevent short-term bleaching of the embedded material due to frequent scanning in a high throughput environment, the value assigned to the embedded calibrant may be date/time stamped and the instrument may issue an instruction to delay subsequent scans for a certain time period. For example, in some embodiments, the drawer is not re-scanned (i.e., re-exposed to the UV excitation light) for 5 minutes to avoid photobleaching. If an interval between scans is less than z seconds, the peak height of the embedded material may not be updated for a subsequent scan. In some embodiments, z is about 300 seconds, about 180 seconds, about 120 seconds, about 60 seconds, about 45 seconds, or about 30 seconds.

In some embodiments, the embedded normalization target and the external calibrant are constructed from the same material. In some embodiments, the embedded normalization target material comprises a plastic, plastic film, glass or fabric doped with an optical brightener. In some embodiments, the material is a plastic selected from the group consisting of polyester, polystyrene and polycarbonate. In some embodiments, the embedded normalization target material is a plastic comprising an organic dye. In another embodiment, the embedded normalization target is an epoxy or epoxy resin comprising a fluorescing compound (i.e., a fluorophore or fluorescent chemical compound).

In some embodiments, the organic dye is a rhodamine. In some embodiments, rhodamine is selected from the group consisting of rhodamine B, rhodamine 6G and sulphorhodamine G (SRG).

In some embodiments, the embedded normalization target is affixed in an optical pathway in the instrument. In some embodiments, the embedded normalization target is affixed to an element in the instrument that is capable of receiving a test strip.

In some embodiments, the optical instrument comprises an optics module for detecting at least one of emitted fluorescent light or emitted reflected light. In another embodiment, the instrument comprises a fixed digital camera like device, positioned such that light emitting from the test device and normalization target is captured in a format that can be analyzed by software in the instrument.

In addition to the exemplary aspects and embodiments described above, further aspects and embodiments will become apparent by reference to the drawings and by study of the following descriptions.

Additional embodiments of the present methods, systems, apparatus, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

DETAILED DESCRIPTION

I. Definitions

Figure 1A:
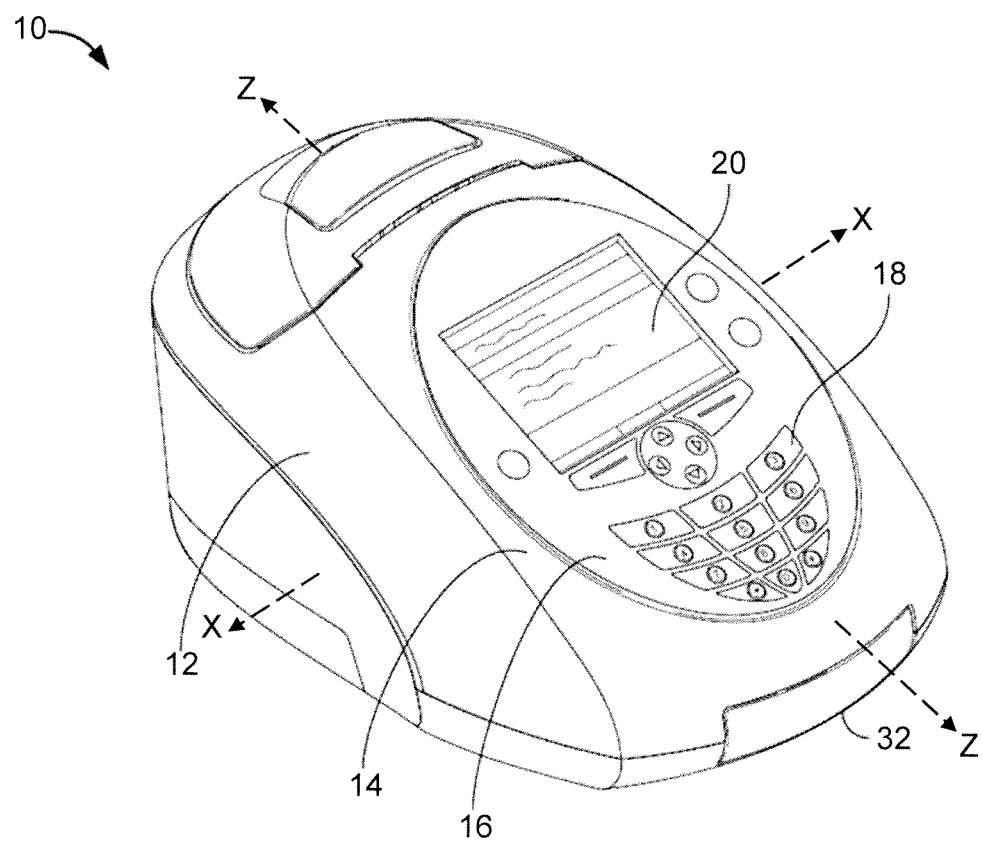
FIGS. 1A-1C are front perspective (FIG. 1A), side (FIG. 1B) and top, partial (FIG. 1C) views of an apparatus, which comprises a drawer that receives a test device, the drawer shown in a closed position (FIG. 1A) and an open position (FIGS. 1B-1C)

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this specification, the singular forms "a," "an," and "the" include plural referents unless the context clearly dictates otherwise. Thus, for example, reference to an "antibody" includes a single antibody as well as two or more of the same or different antibodies, and reference to a "component" includes a single component as well as two or more of the same or different components, and the like.

As used herein, "calibration" refers to the process of comparing a measurement with a standard of known value (sometimes called a "gold standard") and adjusting the result/output measurement system of the measuring instrument in accord with the standard. In some embodiments, a calibration cassette is generated, and calibrated against the gold standard for use of the calibration cassette in an optical analyzer. In some embodiments, the gold standard is fluorescent. In some embodiments, a fluorescent lanthanide target is used as a calibrant. In some embodiments, the fluorescent lanthanide is europium. In some embodiments, the external calibrant is rhodamine. In some embodiments, a "calibration value" is assigned to an external calibrant. In some embodiments, the calibration of an optical analyzer is recorded in the instrument memory. In some embodiments, the calibration value of the instrument represents an overall controlling value for subsequent measurements. In some embodiments, the instrument will be calibrated within each 2-30 day interval.

As used herein, "normalization" refers to a process disclosed herein, by which statistical error and instrument fluctuations are removed from repeated measurements. The present disclosure describes per scan normalization with an internal or "embedded normalization target"/calibrant/reference material. In some embodiments, normalization of the optical instrument refers to a value-assigned calibration material embedded within the instrument. In some embodiments, a "normalization value" is assigned to an embedded normalization target. In some embodiments, the embedded normalization target is fluorescent. In some embodiments, a fluorescent lanthanide or a fluorescent organic dye, such as rhodamine, target is used as a calibrant. In some embodiments, a normalization target value is assigned on a per scan basis. In some embodiments, the normalization value will be reset at each calibration event. A significant change in normalization value from one scan to the next may be flagged as an error and a communication is sent to the user of the instrument.

Accuracy is the degree of closeness of measurements of a quantity to an actual true value.

Precision is the degree to which repeated measurements under unchanged conditions show the same result.

In some embodiments, "assigning a value to an embedded normalization target based on an external calibration value" means to relate an externally calibrated value based on a gold standard with an optically determined value from the embedded normalization target. The process disclosed herein allows the dismissal of errors due to inter-instrument errors, intra-instrument or user errors, and outliers from optical scans and resulting data. With regard to errors based on inter-instrument differences, the external calibrant assures that each instrument responds within a certain percentage (e.g., about 1%, 2%, 3%, 4%, 5%) of signal from the external calibrant and the embedded normalization target attenuates variability in readings for a specific individual instrument. In some embodiments, a scan or image results in capturing peak height data. In some embodiments, data collection after per-scan or per-image normalization eliminates outliers near the limits of the repeatability specification. In some embodiments, per-scan/per-image normalization is not necessary for analyzers demonstrating excellent repeatability. In some embodiments, the presently disclosed methods, systems, analyzers and the like reduce variability to less than system performance specifications without normalization capabilities. In one embodiment, the variability is reduced, for example, by at least about 2%, 3%, 4%, 5%, 8%, 10%, 15%, 20% or 25%.

In some embodiments, assigning a normalization value to an embedded normalization target allows reduction of instrument inter- and intra-variability. In some embodiments, assigning a normalization value to an embedded normalization target allows reduction of "noise," defined as a non-specific, inaccurate and/or imprecise signal. In some embodiments, assigning a normalization value to an embedded normalization target allows the user of an optical analyzer to improve a signal to noise ratio.

"Stable" means that a signal from a standard or target being measured does not degrade in spite of multiple scans. A stable fluorescent target may be embedded in the optical analyzer, for example in a drawer that receives a test strip.

"Scanning in a single scan" means that the optics module scans/reads the normalization target and the test strip in one continuous pass of the optics module along its optical pathway. In some embodiments, the optics module scans/reads the embedded normalization target first and the test strip second in the single scan. In some embodiments, the optics module scans/reads the test strip first and the embedded normalization target second in the single scan.

"Imaging a test strip" means that a digital camera like device using a CCD or CMOS light sensor collects light output data from the test in a way that can be processed into signal data by software in the instrument.

Systems and apparatuses for analysis of samples to aid in medical diagnosis and/or detection of the presence or absence of an analyte in a sample are also disclosed in U.S. Patent Application Publication No. 2013/0230844 and U.S. Patent Application Publication No. 2013/0230845, the disclosure of each incorporated herein by reference herein in its entirety.

Also of interest are the following patents and applications: U.S. Pat. No. 7,521,260, issued 21 Apr. 2009, describing diagnostic test strips and systems for optically reading them that employ "a data analyzer that performs at least one of (a) identifying ones of the light intensity measurements obtained from the test region based on at least one measurement obtained from the at least one reference feature, and (b) generating a control signal modifying at least one operational parameter of the reader based on at least one measurement obtained from the at least one reference feature; U.S. Pat. No. 7,925,445, issued 12 Apr. 2011, describing a read-write assay system; U.S. Pat. No. 8,334,522, issued 18 Dec. 2012, describing optical methods and apparatuses for quantitatively determining the concentration of fluorophores of a substance in a sample; and U.S. Patent Application Publication 2012/0300205 describing a method of normalizing a fluorescence analyzer involving multiple measuring steps.

II. Method to Improve Instrument Precision

In a first aspect, a method for improving the precision of a test result from an instrument that optically detects a signal from a test device is provided. The method, in other embodiments, improves accuracy of a test result. The method, in other embodiments, improves both precision and accuracy of a test result. The method(s) comprise providing an instrument which comprises a normalization target embedded in or on the instrument, directly or indirectly in the pathway of the optical system of the instrument. A signal from the normalization target is obtained each time a signal from a test device is obtained, and the current value of the normalization target signal is compared to a stored value of the normalization target. The signal from the test device can be adjusted or scaled, as needed, based on the current value and stored value of the normalization target. The method will be described in more detail below, and examples of improved precision of test results illustrated. First, however, an exemplary optical instrument (also referred to herein as an apparatus) and exemplary test device are described. In the description below, the test device is exemplified by a lateral flow immunoassay, and is sometimes referred to as a test strip. It will be appreciated that the test device is not intended to be limited to the lateral flow immunoassay test device used to exemplify the system, and a skilled artisan will appreciate that other test devices, such as microfluidic devices, immunoassays other than lateral flow based immunoassays, are contemplated.

Apparatus

Figure 1B:
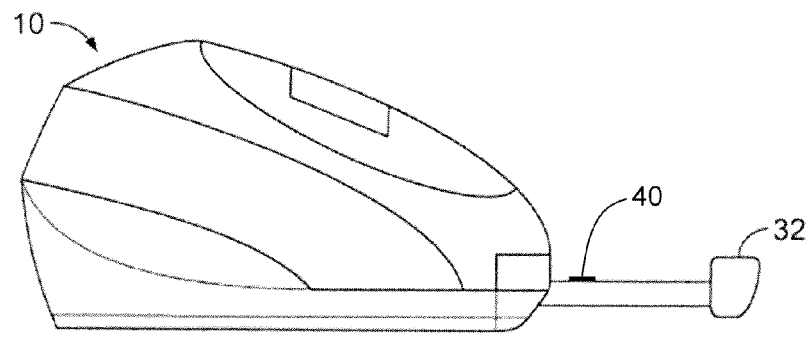
Figure 1C:
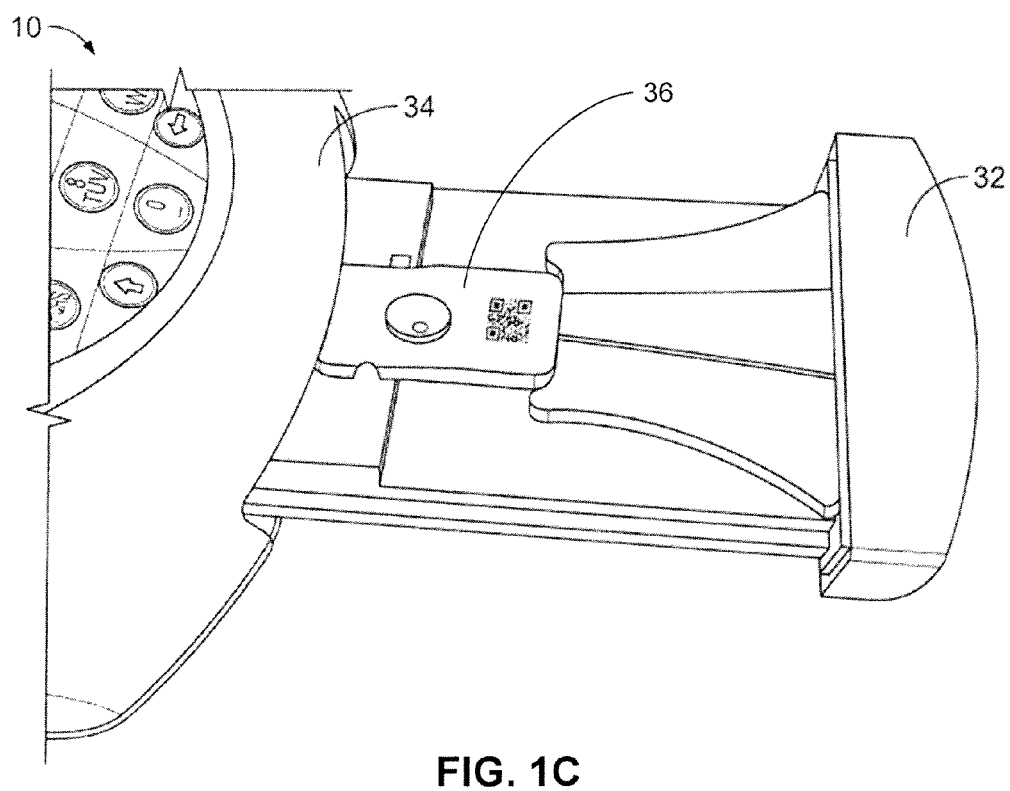

An exemplary apparatus contemplated for use in the method herein is described in U.S. Patent Application Publication No. 2013/0230844 and in U.S. Patent Application Publication No. 2013/0230845, each of which is incorporated by reference herein in its entirety. FIGS. 1A-1C are views of an exemplary apparatus, which will not be briefly described.

FIG. 1A is a perspective view of apparatus 10 which includes a housing 12 that encloses an optics system, electronics software, and other components of the apparatus. A front side 14 of the apparatus includes a user interface 16 that may include, for example, a key pad 18 and a display screen 20. The apparatus also includes a drawer 32 movable between open and closed positions, as shown in FIG. 1A in its closed position and in FIGS. 1B-1C in its open position. In the embodiment shown, the drawer is positioned on a front edge 34 of the apparatus. It will be appreciated that the drawer could also be positioned on either side of the apparatus. The drawer can move between its open and closed positions by a mechanical mechanism, such as a latch and spring mechanism, or in response to a user activating a key on the front or face of the apparatus, such as an "open drawer" or "eject test device" button. In one embodiment, the drawer is moved into its closed position after insertion of a test device manually by a user, or in response to a user activating a key or button on the apparatus. The drawer is configured to receive an immunoassay test device, such as test device 36, further described below. Within the drawer, in one embodiment, is a distinct region, for example a depression, sized to receive the test device. During operation of the apparatus, the test device remains in a stationary position in the drawer, and therefore is positioned with precision in the apparatus for precise interaction with a movable optics module.

The apparatus also includes a normalization target disposed in or on the apparatus. The normalization target, in a preferred embodiment, is directly in the optical pathway of the optics module (described below), and an exemplary position of the normalization target 40 is indicted in FIG. 1B. Normalization target 40, in one embodiment, is disposed or embedded on drawer 32, and in a position that remains exposed to the optics module when a test device is inserted in the drawer. It will be appreciated that the normalization target 40 can also be disposed or embedded in the instrument indirectly in the optical pathway, such as on a side wall or positioning arm of the instrument, and mirrors or other techniques can be used to achieve interaction of the normalization target with the optics module. The normalization target generally takes the form of a material that is deposited on the instrument or embedded in the instrument in a position for interaction with the optical system. The material is one that responds to a source of excitation light in the optics system by emitting energy in the form of signal detectable by a photodetector in the optics system. Exemplary materials are discussed below.

In general, the apparatus will comprise a drawer movable between an open position and a closed position where the drawer is contained within the housing; an optional bar code scanner positioned in the housing for reading an encoded label on a test assay (or test device) to be inserted into the apparatus; a carriage movably mounted in the housing, the carriage comprising a source of excitation light and a photodetector for detecting energy emitted; drive electronics to move the carriage sequentially from a first position to a final position, and a plurality of positions there between, wherein the carriage has a dwell time at each of said plurality of positions between the first and final positions; a processor for control of the apparatus, wherein the processor comprises a software program that processes data obtained from the photodetector by generating a data array comprised of emitted signal at each incremental position between the first and final positions, taking the first derivative of the data array to form a derivative data set, wherein a first maximal value in the derivative data set corresponds to a maximum signal from a reference line or a control line on the test device, and the position in the derivate data array of the first maximal value determines the position of data from the analyte-specific test line.

In some embodiments, when the instrument is first powered on, the software runs a check for the time and date stamp of the normalization value stored in memory that was assigned to the embedded normalization target, and (i) if an assigned normalization value is found, and it is less than a certain age, this assigned normalization value is used for adjusting (or scaling) a test signal to be obtained, or (ii) if an assigned normalization value is not found in memory, or if the previously assigned normalization value is of a certain age, the user is instructed to proceed to scan and assign a new or updated normalization value to the embedded normalization target. In other embodiments, if an assigned normalization target value changes more than a pre-defined amount relative to an assigned normalization value stored in memory, then a communication is sent to the user, which may indicate that the instrument drawer should be removed and cleaned, or that the newly assigned normalization value is beyond a certain limit with respect to the external calibrant, and/or that the instrument should be recalibrated with a gold standard. In some embodiments, there may be no communication to the user, and the instrument may enter a lock-down mode, forcing recalibration and/or renormalization. In some embodiments, a barcode inside the instrument may be present which correlates with the normalization target such that the instrument will recognize different drawers or normalization targets.

As mentioned above, the apparatus includes a movable optics system in the apparatus, to scan the stationary test device inserted into the apparatus. The microprocessor-controlled optics system is positioned within the housing of the apparatus such that it moves along the longitudinal axis (along the line denoted z-z in FIG. 1A) from a home or start position to a final position. The optics system includes an optics module comprised of a carriage mounted on a track (e.g., lead screw), the carriage movable by an electric motor or actuator within the optics system of the apparatus. Secured to the carriage, and part of the movable optics module, are an illumination source and a detector, such as a photodiode. The illumination source is typically mounted to illuminate the test device, for example perpendicular to the test device, and the detector oriented at an angle to collect emission from the test device. In some embodiments, a photodiode is oriented at 40° relative to the test device, and more generally the detector can be oriented at an angle of between about 20°-75° relative to the surface of the test device. In some embodiments, the optics module includes a single element optical detector (that is, an array of optical detectors is not present) and a single illumination source. The optics module can also comprise one or more filters, and can include a filter, in some instances a long pass filter, on the emission side of the illumination source, and a filter positioned between the test device and the detector. In some embodiments, the illumination source emits UV light at a wavelength that matches the excitation wavelength of a label in the test device. In some embodiments, the illumination source is a light emitting diode (LED) that has a peak emission at 365 nm, more generally of between about 320-390 nm or 325-380 nm. In this embodiment, the band pass or interference filter positioned in the optical path from the LED to the test device transmits light between 340-400 nm or between 310-315 nm.

In some embodiments, the photodetector is a broad band detector suitable to detect light at the wavelength emitted from the label in the test device. In some embodiments, the photodetector is a single-element photodetector (i.e., is not an array of photodetectors). In some embodiments, the label is or contains a fluorescent, luminescent, chemiluminescent compound. As will be described below, an exemplary fluorescent label is a lanthanide ion, such as europium, samarium, terbium and holmium, which each fluoresce at specific wavelengths. A filter may be positioned in the optical path between the test device and the detector, in some embodiments, and can transmit light above about 515 nm for detection by the detector. A skilled artisan will appreciate that a variety of filters are known in the art (longpass, shortpass, bandpass, etc.) and can be selected according to the wavelengths of light desired to excite a label and the wavelength of light desired for detection.

The apparatus, in some embodiments, includes a temperature sensing means, and in some embodiments, includes at least two temperature sensing devices housed within the housing of the apparatus. A first internal temperature sensor is positioned to detect the temperature in the region associated with the optics system and a second internal temperature sensor is positioned elsewhere in the apparatus away from any internally generated heat source in order to detect ambient temperature of the environment in which the apparatus is operated.

The apparatus includes internal memory storage with necessary software for operation and for storage of data collected from sample analysis. By the SIM port or by an external computer (wireless or wired attachment), data can be exported from the apparatus or imported to the apparatus.

As mentioned above, the apparatus may be equipped with ports for attachment to optional external devices. An external bar code scanner may be attached to the apparatus. Such a bar code scanner interfaces with the apparatus via a suitable data port provided on the apparatus. Externally attached devices ease transfer of data into and from the apparatus, and can eliminate user keyboard input, permitting accurate data input into the apparatus regarding a test to be analyzed or patient or sample information. In some embodiments, a barcode scanner external is attachable via PS-2 port on the apparatus and is capable of reading a linear or 1D bar code. In some embodiments, the apparatus is wireless or wired connected to a device for delivering data to a third party.

External Calibrant and Normalization Target

As described above, the apparatus comprises an optics system comprised of an optics module that includes a light source, which in some embodiments is an LED light source with a peak emission at 365 nm. The detector for the emitted signal, such as fluorescent light from a label in a test strip, is a photodiode with filters to ensure that the light from the fluorescent reagent is not contaminated by ambient nor excitation light. Signal from the photodiode is translated through an analog to a digital converter where the digital signal is processed by a microprocessor in the apparatus into a test result. To ensure consistent light output, the LED has a feedback loop whereby the optics system monitors the light output of the LED and triggers an adjustment of the electrical current to the LED to ensure a consistent intensity of the excitation light beam in real time. To further ensure that signal drift is controlled, the apparatus has a calibration algorithm that enables the user to insert an external calibrant specifically designed for the apparatus and provided with the apparatus. The apparatus also includes a normalization target positioned for interaction with the optics system, where signal from the normalization target is detected each time signal is detected from a test device inserted into the instrument for detection of an analyte.

In another embodiment, the apparatus comprises, rather than an optics module, a fixed digital camera like device. The imaging device is located such that light emitting from the test device is captured in a format that can be analyzed by software in the apparatus.

Figure 2:
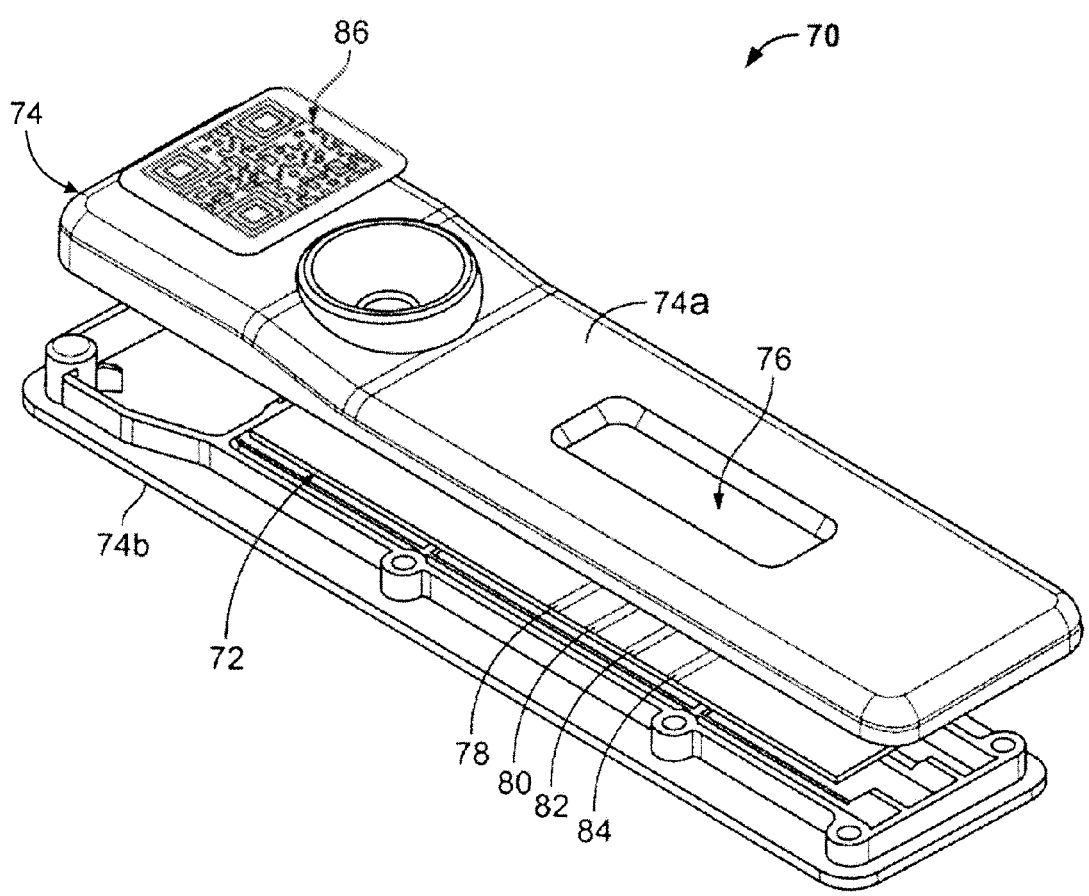
FIG. 2 is a view of a calibration cassette.

An exemplary external calibrant, in the form of a calibration cassette, is illustrated in FIG. 2. Calibration cassette 70 comprised of a calibration strip 72 secured within an optional housing member, such as housing member 74 which is separable in this embodiment into upper member 74a and lower member 74b. A window 76 in upper housing member 74a is provided so that the optics system in the apparatus can interact with one or more lines on the calibration strip. The calibration strip can comprise one or more lines, and in various embodiments, comprises two or more lines, three or more lines or four or more lines. In some embodiments, the calibration strip comprises at least two lines, at least three lines, or at least four lines. The embodiment illustrated in FIG. 2 shows a calibration strip with four lines, identified as 78, 80, 82 and 84, and referred to herein below as calibration lines or calibration test lines. The calibration lines are positioned on the strip relative to the housing to be visible through the window when the strip is secured within the housing.

In some embodiments, the normalization target and/or calibration strip is/are comprised of a material that fluoresces upon excitation by light from the illumination source in the optics system of the apparatus at a wavelength detectable by the photodiode subsequent to passage through any filter(s) in the light path of the photodiode. In some embodiments, the normalization target and/or calibration strip is comprised of a material that fluoresces, and the calibration lines or normalization target are defined by masking. For example, the fluorescing material can be silk-screened with a material that blocks light entering and leaving the one or more calibration lines exposed. Alternatively, a fluorescing material can be deposited in discrete lines onto a non-fluorescing material to form the normalization target or calibration lines of the external calibrant.

In some embodiments, the fluorescing material is a fluorescent whitening agent, also known as fluorescence brightners, deposited on or dispersed in a support material. Exemplary fluorescent whitening agents optical brightener are dyes that absorb light in generally the ultraviolet and violet range (340-370 nm) of the electromagnetic spectrum and re-emit light in the blue region (typically 420-470 nm). Exemplary optical brighteners include compounds such as stilbenes (di-, tetra, or hexa-sulfonated), coumarins, imidazolines, diazoles, triazoles, benzoxazolines, biphenyl-stilbenes. A specific exemplary class of compounds are thiophenediyl benzoxazole compounds, and a specific exemplary fluorescent whitening agent is 2,5-thiophenediylbis(5-tert-butyl-1,3-benzoxazole), an optical brightener. Exemplary support materials include polymers, and particularly plastics, such as polymethylmethacrylates and polyesters, in particular biaxially oriented polyester. The whitening agent can be polymerized with the support material during manufacture of the polymeric support material, or can be deposited onto the polymeric support after its manufacture. In some embodiments, the fluorescing material forming the one or more calibration lines or normalization target fluoresces between 500-650 nm when excited.

The calibration cassette can optionally include a label, such as bar code 86 on the cassette in FIG. 2. In some embodiments, the bar code is a linear or a two-dimensional bar code with information, for example, to confirm for the apparatus that the cassette is a calibration cassette and with information regarding an expiration date for the cassette.

The calibration cassette is dimensioned to fit within the drawer of the apparatus, for interaction with the optics system. The calibration cassette when inserted into the instrument does not block the normalization target that is deposited in or embedded internally in the instrument for interaction with the optic system, so that during when the optics system moves in a single, continuous scan from its first to final position, it interacts with both the external calibrant and the normalization target. Signal emitted from the external calibrant and the normalization target are detected and stored in instrument memory.

A user of the apparatus, typically when prompted by the apparatus at a regular, defined period, such as every 30 days, or once a month, or once every two months, etc., inserts the external calibrant/calibration cassette into the drawer of the apparatus. The internal bar code reader within the apparatus transfers the information on the barcode of the calibration cassette to the processor in the analyzer. It will be appreciated that the internal bar code reader is an optional feature, as the information on the bar code label can be entered into the apparatus by a user using the key pad or via an external bar code scanner. From this information, the instrument will confirm that a calibration cassette has been inserted into the analyzer, provide target signals the instrument uses for comparison to actual signals obtained for the calibration lines on the calibration strip, and provide the expiration date of the calibration cassette. The instrument then activates the optics system to initiate illumination of the calibration cassette, and specifically sequential illumination of each of the calibration lines visible within the calibration cassette window. The instrument then detects the fluorescent signal from each of the calibration lines and stores the signal in memory. The instrument also detected the fluorescent signal from the normalization target embedded in or on the instrument.

With regard to the signal from the external calibrant, the detected signal for each of two of the calibration lines from the external calibrant is compared to the expected signal (e.g., a signal value stored in memory or provided on the bar code of the external calibrant) for that calibration line. If the detected signal for each of two of the calibration lines is within a predefined range of the target signal, for example within (+/−) 1.75, 2%, 2.25%, 2.5% or 3%, then the calibration of the analyzer is valid and no adjustments to the apparatus are needed. This calibration check event is recorded and stored in the memory of the apparatus. If the detected signal for either or both of two of the calibration lines of the external calibrant is outside the predefined range of the target signal, but not outside of a maximum predefined range, for example outside +/−3.25%, +/−3.5%, +/−3.75% or +/−4% of a predefined target signal for a specific line, the processer in the analyzer activates an algorithm to self-calibrate using a third or different calibration line on the calibration test strip. Information for the expected signal from this third line is also in the barcode information and was conveyed to the apparatus upon insertion of the calibration cassette and scanning of the bar code. When the signal for this third calibration line is within a defined acceptable range, the analyzer again reads the first two calibration lines to confirm that the expected target signal is detected for these two lines. If the signal is outside the maximum range, the analyzer cannot recalibrate itself, and the system generates an error message that is displayed to the user.

With regard to the signal from the normalization target, in embodiments where the material of the normalization target is identical to the material of the external calibrant, a normalization value is assigned to the normalization target based on the signal from the external calibrant. In embodiments where the material of the normalization target is different from the material of the external calibrant, a normalization value is assigned to the normalization target based on signal from the normalization target that is adjusted by a factor stored in instrument memory that accounts for expected signal differences between the external calibrant material and the normalization target material. The normalization value assigned to the normalization target is stored in instrument memory.

Test Device: Exemplary Lateral Flow Immunoassay

Figure 3:
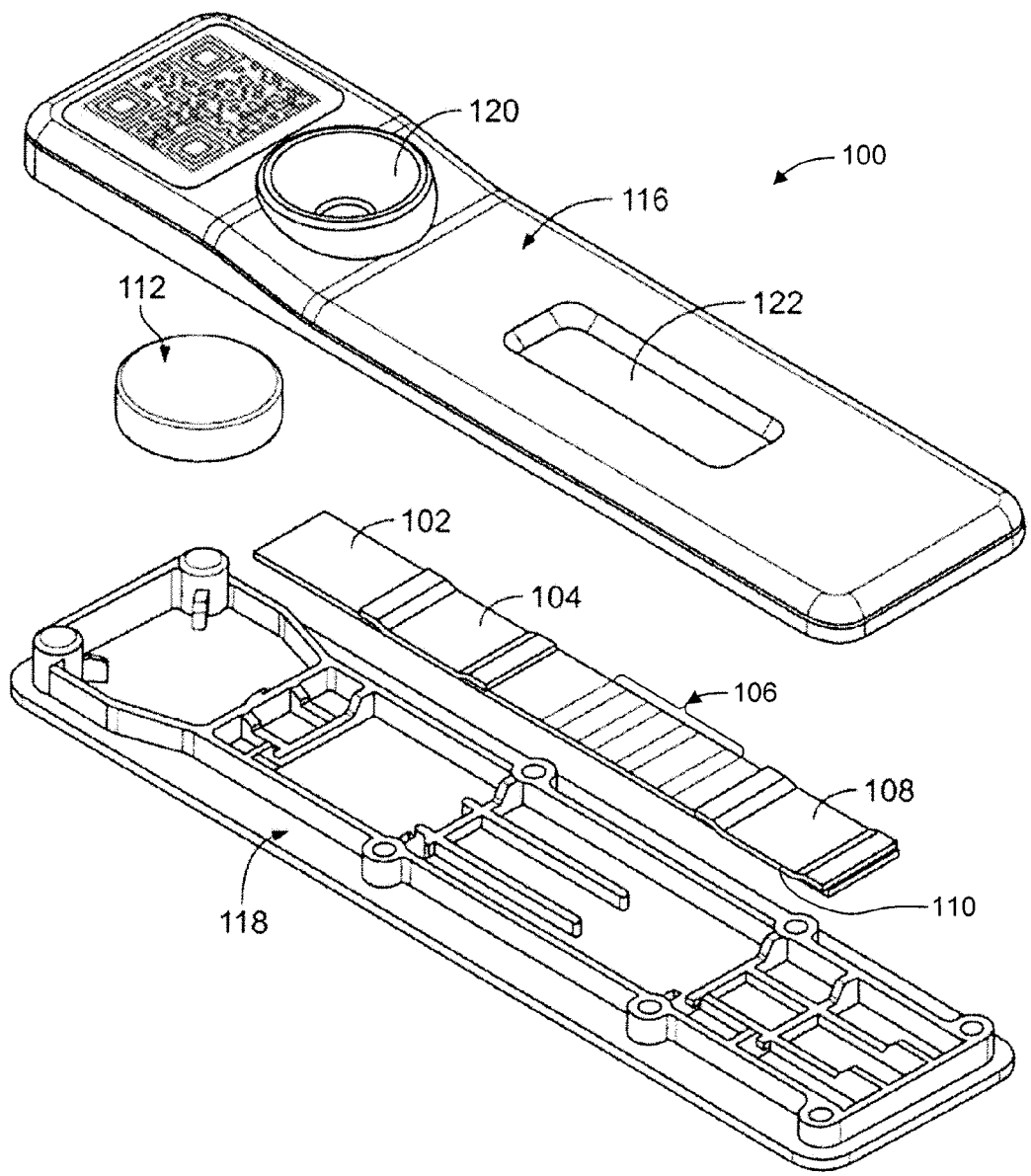
FIG. 3 is an illustration of a test device wherein a test strip is enclosed in an optional housing sized for insertion into a drawer of an apparatus.

The apparatus described above is designed to receive and interact with a test device, and an example of a test device is shown in FIG. 3. In FIG. 3, a test device comprising a test strip enclosed in an optional housing that is sized for insertion into a drawer of an apparatus is shown. The test device is exemplified in the drawings below by a lateral flow test immunoassay, however it will be appreciated that a lateral flow immunoassay is exemplary of test devices suitable for interaction with the apparatus.

Test device 100 is comprised of, in sequence, a sample pad 102, a label pad 104, one or more lines indicated collectively at 106 and selected from a test line, a control line and a reference line, and an absorbent pad 108. In some embodiments, a support member 110 is provided, and each or some of the sample pad, label pad, lines and absorbent pad are disposed on the support member. In some embodiments, the test device additionally includes a desiccant portion, which can be positioned on the support member of the test device, and in some embodiments is disposed on the support member downstream of the absorbent pad, as described in U.S. Patent Application Publication No. 2008/0311002, incorporated by reference herein, or can take the form of a discrete component, physically separate from the test strip, inserted into a housing member that contains the test strip, such as desiccant 112.

In some embodiments, the test strip is enclosed in an optional housing, sometimes referred to herein as a cassette. The optional housing may be comprised of an upper member 116 and a lower member 118 that fit together to form a housing. The lower member may include architectural features that define dimensioned regions for receiving the test strip and an optional desiccant. The upper housing member includes at least two openings, a first sample input port 120 and a viewing window 122. The sample input port is disposed directly above the sample pad on the test strip, so that a sample dispensed into the sample input port contact the sample pad for flow along the test strip. The sample input port can include a bowl portion to receive a liquid sample into the port. The viewing window is positioned to reveal the lines in the test strip, so the optics system in the apparatus can interact with the lines.

In some embodiments, a bar code label is affixed to the upper housing member. It will be appreciated that the bar code label can be positioned elsewhere on the housing, and is positioned for interaction with the internal bar code scanner positioned within the apparatus. In some embodiments, the bar code label is a 2D bar code, encoding information, for example, regarding the assay test strip, such as the pathogen/analyte the test strip is designed to detect (Flu A/B, Strep A, RSV, others listed below, etc.) which informs the apparatus what protocol in memory to initiate for scanning the test strip; a unique test serial number so that the apparatus will not read same test strip twice. In some embodiments, the information contained in the bar code does not include information related to the patient or the sample type, and is limited to information about the test strip.

It will be appreciated that the test device illustrated in FIG. 3 is exemplary of lateral flow test devices in general. The test strip can be configured uniquely for any given analyte, and the external housing is optional, and if present, need not be a cassette housing but can be a flexible laminate, such as that disclosed in U.S. Patent Application Publication No. 2009/02263854 and shown in Design Pat. No. D606664, both of which are incorporated by reference herein. The system is such that the drawer in the apparatus and the test device are dimensioned to receive the test device in the drawer, and the optics system in the apparatus has a movement path the scans the necessary regions of the test device.

In that regard, an exemplary test strip may include a sample receiving zone in fluid communication with a label zone. A fluid sample placed on or in the sample zone flows by capillary action from the sample zone in a downstream direction. A label zone is in fluid communication with at least a test line and a control line or a reference line. In some embodiments, the label zone is in fluid communication with a negative control line, an analyte test line, an optional second analyte test line, and a reference line. The two or more lines are in fluid communication with an absorbent zone. That is, the label zone is downstream from the sample zone, and the series of control and test lines are downstream from the label zone, and the absorbent pad is downstream from the portion of the test strip on which the lines are positioned. A region between the downstream edge of the most downstream analyte-specific test line and the upstream edge of the absorbent pad is a procedural control zone. A reference line is within the procedural control zone. As will be described below, the procedural control zone, and in particular the reference line therein, (i) ascertains whether sample flow along the test strip occurred based on its RLU signal (emission), and (ii) may be used by the analyzer (or more properly, an algorithm stored within the analyzer) to determine the relative locations of the other lines (control, if present, and analyte-specific test line(s)) on the test strip. The reference line may also be used to ascertain a cut-off value, as will be described below, to render the immunoassay insensitive to incubation time, and in particular insensitive to incubation time over a period of 1-15 minutes, a period of 1-12 minutes, a period of 1-10 minutes or a period of 2-10 minutes. Materials for construction of each of the zones is well known in the art, and includes, for example, a glass fiber material for the sample zone, a nitrocellulose material on which the two or more lines are positioned.

The sample zone receives the sample suspected of containing an analyte of interest control its flow into the label zone. The label zone, in some embodiments, contains two dried conjugates that are comprised of particles containing a lanthanide element. The lanthanide materials include the fifteen elements lanthanum, cerium, praseodymium, neodymium, promethium, samarium, europium, gadolinium, terbium, dysprosium, holmium, erbium, ytterbium, lutetium, and yttrium. In some embodiments, the dried conjugates are particles which are polystyrene particles or microparticles (particles less than about 1,000 micrometers in diameter, in some instances less than about 500 micrometers in diameter, in some instances less than 200, 150 or 100 micrometers in diameter) containing a luminescent or fluorescent lanthanide, wherein in some embodiments, the lanthanide is europium. In some embodiments, the lanthanide is a chelated europium. The microparticles, in some embodiments, have a core of a lanthanide material with a polymeric coating, such as an europium core with polystyrene coating. A binding partner for the analyte(s) of interest in the sample is/are attached to or associated with the outer surface of the microparticles. In some embodiments, the binding partner for the analyte(s) of interest is an antibody, a monoclonal antibody or a polyclonal antibody. A skilled artisan will appreciate that other binding partners can be selected, and can include complexes such as a biotin and strepavidin complex. Upon entering the label zone, the liquid sample hydrates, suspends and mobilizes the dried microparticle-antibody conjugates and carries the conjugates together with the sample downstream on the test strip to the control or reference and test lines disposed on the nitrocellulose strip. If an analyte of interest is present in the sample, it will bind to its respective conjugate as the specimen and microparticles flow from the label zone onto the surface of the nitrocellulose. In some embodiments, this flowing mixture will then encounter negative control line. The negative control line may be comprised of mouse immunoglobulin (IgG) to enable detection of non-specific binding of the conjugates to the immunoglobulin, thus approximating the level of non-specific binding that will occur at the downstream test line(s). The signal generated at this negative control line is used to help ensure that high non-specific binding at the analyte-specific test line does not lead to false positive results.

For example, as the sample and microparticle-antibody conjugates continue to flow downstream, if the analyte of interest is present in the sample, the fluorescent microparticle-antibody conjugate, which is now bound with antigen/analyte of interest, will bind to the specific binding member for the analyte of interest that is immobilized at the test line(s). In some embodiments, a single test line is present on the test strip. In some embodiments, at least two, or two or more test lines are present on the strip. By way of example, a test strip intended for detection and/or discrimination of influenza A and influenza B can include a first test line to detect influenza A and a second test line to detect influenza B. Microparticle-antibody conjugates comprised of microparticles coated with antibodies specific for influenza A and microparticles coated with antibodies specific for influenza B may be included in the label zone, and in some embodiments, downstream of the negative control line. A first test line for influenza A and a second test line for influenza B can be disposed downstream of the label zone. The first test line for influenza A comprises a monoclonal or polyclonal antibody to a determinant on the nucleoprotein of influenza A and the second test line for influenza B comprises a monoclonal or polyclonal antibody to a determinant on the nucleoprotein of influenza B. If antigen is present in the sample, a typical immunoassay sandwich will form on the respective test line that matches the antigen in the sample.

The microparticle-antibody conjugates that do not bind to the negative control line or to a test line continue to flow by capillary action downstream, and the remaining sample encounters the reference line, in some embodiments proceeding into the absorbent pad.

Test Procedure and Instrument Operation

Figure 4:
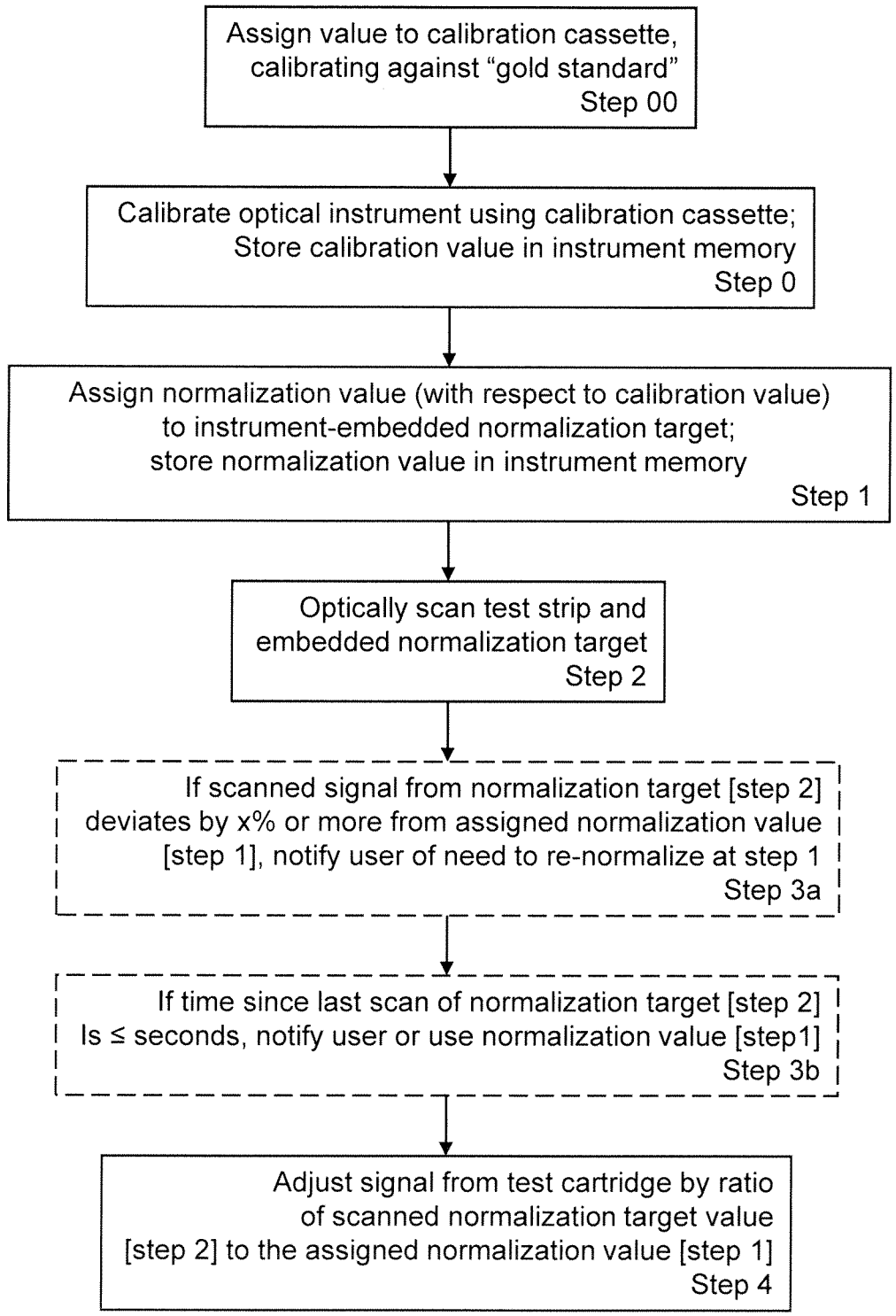
FIG. 4 is a schematic showing steps involved in calibrating an apparatus, and in detecting the presence or absence of an analyte in a sample via test device inserted into an apparatus with a normalization target.

FIG. 4 is a flow chart showing steps involved in calibrating an apparatus using an external calibrant, and in detecting the presence or absence of an analyte in a sample via test device inserted into an apparatus with a normalization target. In step 00, the external calibrant is calibrated using a recognized measurement standard (often referred to in the industry as a 'gold standard'). Instruments that demonstrate a signal output for the external calibrant material that is at or within a fixed range of the mean signal from a manufacturing lot of instruments are selected to serve as the 'gold' or calibration instruments. These gold instruments are used to assign a value to the external calibrant.

Once the external calibrant has a value assigned to it based on a gold standard, the external calibrant is used to calibrate a specific instrument. The external calibrant, as denoted in Step 0 of FIG. 4, is inserted into the instrument, signal from the external calibrant is detected upon excitation by the optics system, and the detected signal compared to the expected value of the external calibrant, which in some embodiments can be a value stored on a barcode on the external calibrant that is read by the instrument. By way of example, and with reference to the exemplary external calibration cassette of FIG. 2, if the observed values from line 1 and line 4 (peak 1 and peak 4) are within a pre-determined range (e.g., 2%) of the expected external calibrant value the instrument is deemed to be calibrated, and need not be recalibrated. If either of the observed values is greater than the pre-determined range (e.g., 2%) but less than a certain amount, e.g., 10%, different from the expected calibrant value then the instrument recalibrates based on the difference between the observed value for line 3/peak 3 versus the expected external calibrant value for line 3/peak 3. The instrument calibration factor is changed according to the line 3/peak 3 measurement and is stored in instrument memory as the external calibrant value.

Next, with the external calibrant inserted into the machine, the optical system excites the external calibrant and the instrument-embedded normalization target. Signal emitted from the normalization target is detected and signal from the external calibrant is detected, the signals preferably obtained in a single scan of the optical system as it moves uninterrupted along the optical pathway. A normalization value is assigned to the normalization target, based on the detected signal for the normalization target and the detected signal of the external calibrant, as indicated in Step 1 of FIG. 4. The normalization value of the normalization target is stored in instrument memory. A comparison is made of the percent difference of the external calibrant signal (peak height) in comparison to the signal (peak heights) from the normalization target observed versus stored value. If this relative difference is larger than a preset value, the user is prompted to rerun calibration with the external calibrant, clean the normalization target, or replace the external calibrant.

With continued reference to FIG. 4, a test device comprising a sample suspected of containing an analyte is provided, and the test device with the sample is inserted into the instrument. An optical scan of the test device is initiated by the user, and additional details on the sequence of events that occur within the instrument upon initiation of a test scan of a test device are provided in FIG. 5. As denoted in Step 2 of FIG. 4, the optical system of the instrument scans the test device and the embedded normalization target, preferably in a single, continuous, uninterrupted scan of the optics module from its start position to its final position. Signal emitted from the normalization target is detected, as is signal from the test line(s), control and reference lines (if present) on the test device. If the measured signal from the normalization target deviates by x % or more from the assigned normalization value stored in instrument memory, the instrument is programmed to communicate to the user that the instrument may require re-normalization (Step 3a, FIG. 4). In this situation, a user would remove the test device and insert the external calibrant and initiation a scan of the optics system, to assign an updated normalization value to the normalization target based on a scan of the external calibrant and the normalization target (e.g., Step 1 of FIG. 4 is performed). The value of x can be present in the instrument software, and atypical value of x is 0.5%, 1%, 1.5%, 2%, 3%, 4%, 5%, 6%, 7%, 8%, 9%, 10%, 12%, 14%, 15%, 18% or 20%. The software of the instrument also determines the time lapse between the current scan and the time since the last or previous scan of the normalization target. If the time since the last scan of the normalization target is less than or equal to z seconds, the instrument is programmed to use the normalization value from the prior scan of the embedded normalization target (Step 3b, FIG. 4). This optional feature is to avoid effects from photobleaching of the normalization target. The value of z will depend on the material of the normalization target, and is a value that can be programmed into the software of the instrument or provided on a bar code external to the instrument. The value of z can be, for example, between 5-360 seconds, or 10-300 seconds, or 15-300 seconds, or 30-360 seconds. In another embodiment, a the value of z is less than or equal to 300 seconds, 180 seconds, 120 seconds, 60 seconds, 45 seconds, or 30 seconds.

Signal detected from the one or more lines on the test device may be adjusted by a scaling factor that is determined from the scanned normalization value and the assigned normalization value (stored in instrument memory), as indicated in Step 4 of FIG. 4. In some embodiments, the scaling factor may be equal to the ratio of the scanned normalization target value gained from Step 2 to the normalization value assigned in Step 1.

Figure 5:
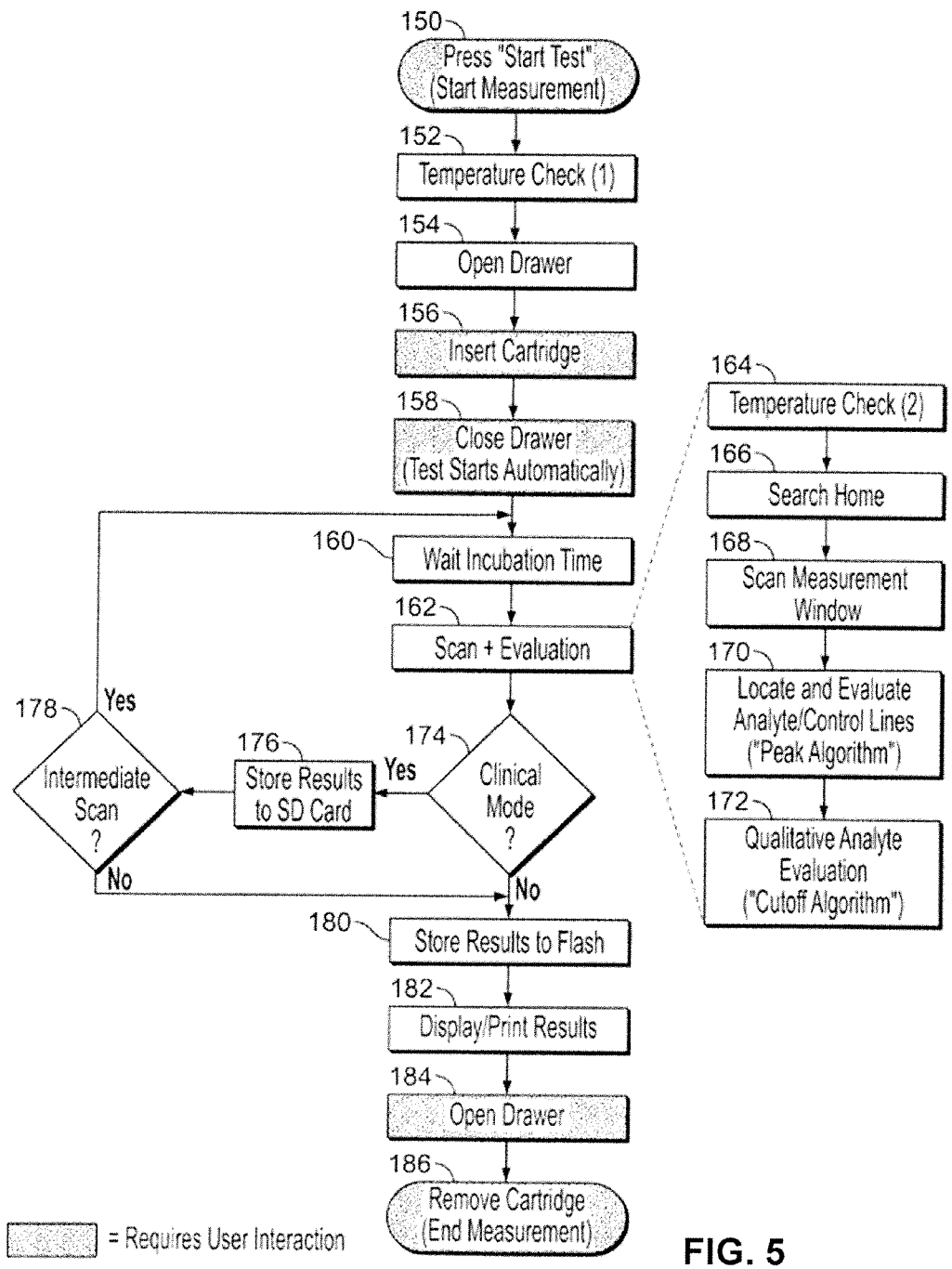
FIG. 5 shows the sequence of events in one embodiment of a measurement procedure where an apparatus as described herein interacts with a test device, wherein the optical system of the apparatus scans the test device and a normalization target to report to a user the presence, absence and/or amount of analyte in a sample.

FIG. 5 shows the sequence of events in one embodiment of a measurement procedure where an apparatus as described herein interacts with a test device, wherein the optical system of the apparatus scans the test device and a normalization target to report to a user the presence, absence and/or amount of analyte in a sample. To initiate a scan of a test device, the apparatus is powered-on if needed and the toggle switch to initiate the apparatus software is activated. Prior to inserting the test device with sample into the apparatus, using the optional external bar code reader information about the user, the sample, the patient, etc. can be scanned into the apparatus memory. With reference to FIG. 6, a "start test" button on the apparatus or on the touch screen is pressed, 150, to start a measurement of a test device. The apparatus takes an optional temperature reading, 152, and then automatically opens the drawer in the apparatus, 154, to receive the test device on which a sample has been dispensed onto the sample pad. The test device with loaded sample is inserted into the drawer, 156, and the drawer is closed manually, 158, with gentle pressure by the user. As the drawer closes, one or more positioning arms press against the test device to position it in the drawer in a precise location that is consistent from test to test. The optics shield within the apparatus is positioned to protect the optics system and its movable optics module from any liquid sample that may splash from the sample input port when the drawer closes.

Closure of the drawer initiates a sequence of events, 158, comprised of the following: The internal bar code reader scans the bar code on the test device and receives information regarding the assay type (e.g., influenza A/B, hCG, Strep A, RSV, etc.), the serial number and the expiration date of the test device, optical cut-off information for the assay type, and any other information included on the bar code secured to the test device. In some embodiments, a mirror is positioned to facilitate interaction of the light beam from the internal bar code scanner and the bar code label on the test device. It will be appreciated that the internal bar code reader is an optional feature, as the information on the bar code label can be entered into the apparatus by a user using the key pad or via an external bar code scanner. Based on the test assay type discerned from the information on the bar code label or otherwise provided to the apparatus processor, the apparatus initiates an algorithm stored in the apparatus's memory for the assay for which the test device is designed, and based on user defined selection of read-now mode or walk-away mode, a protocol stored in memory initiates. In walk-away mode the apparatus incubates for a period of time, 160, prior to initiating a scan of the test device, 162; in read-now mode the apparatus does not wait for the preset incubation time for that particular assay, and immediately begins a scan of the test device, 162.

The scan and evaluation of the test device and the embedded normalization target, 162, comprises another optional temperature check, 164, at the same or different position from the first temperature check 152. The initiated algorithm activates the optics system, including the stepper motor that moves the optics module with respect to the test device that is stationary in the apparatus. The optics system searches for its home position, 166, (described below) and then conducts a scan of the measurement window, 168, in the housing of the test device through which the reference/control and test line(s) are visible. This scan also includes a scan of the normalization target. The motor in the optics system moves the optics module incrementally along an optical pathway between a start position and to a final position; the optical pathway including the normalization target and the length of the measurement window in the test device in accord with parameters defined by the algorithm for the particular assay being conducted. The optics module is moved in incremental steps by the motor in the optics system along the optical pathway, typically in a downstream to upstream direction with respect to sample fluid flow on the test strip, wherein the optics carriage stops at each incremental step or position to illuminate the position, and detect emitted light after illumination at that position, before advancing upstream to the next position.

After collection of emitted light at each of the plurality of incremental positions along the length of the test window, the algorithm locates and evaluates the data in the data array that is associated with the signal emitted from the normalization target, the test lines, control and reference lines (if present), 170, and conducts a qualitative, semi-quantitative or quantitative analyte evaluation using a cut-off algorithm, 172.

The algorithm then determines whether the test is a clinical test, an external control or a calibration test, 174, and if the determination is yes (based on information provided on the test device bar code or based on user input information), the results are stored to memory, 176, such as on the SD card or in the apparatus memory. If the test is not a clinical test, then results are stored to flash memory, 180, and displayed and/or printed, 182. The drawer is then opened, 184, by the apparatus or by the user at the end of the measurement sequence for the user to remove the test device, 186.

It will be appreciated that the test sequence is easily varied by simply varying the programming in the software programs in the device, to alter the sequence of events, time allocated to each event, etc., in a measurement procedure.

The measurement sequence by the optics system can include activating the motor that moves the optics module, and the optics module finding its home position. At a first position along the optical read path that corresponds with the test window on the test device inserted in the apparatus, the illumination source in the optics module is turned on and then off, and during the off period fluorescent emission is detected by the photodetector in the optics module. The detected emission is stored in memory, and the motor in the optics system advances the optics module a fixed amount to its next position. The path the optics system follows permits excitation and emission of the normalization target, directly or indirectly, and of the test device. After completion of a predefined number of incremental steps along the length of the optical pathway and capture of light emission at each step, the optics module is returned to its home position by the motor, and the motor is powered off. It will be appreciated from this description, that in some embodiments, the apparatus comprises a dynamic optics module of an illumination source and a photodetector, wherein the module is static during an illumination/detection sequence and resumes dynamic movement thereafter. It will also be appreciated that the dark reading, i.e, detected emission during the off, or dark period, of the illumination-detection sequence, is utilized for purposes of baseline and background and not for time-resolved fluorescence.

The algorithm stored in apparatus memory for that particular assay then searches the data array for the peak emissions for each of the normalization target, the test line(s) and reference lines to calculate line intensities of peak area or peak height. The algorithm calculates results from the data array and stores the results to memory, such as on the SD card inserted into the device. The calculated result can be displayed to the screen on the apparatus, or prompted to be printed by the user, or stored in flash memory if needed. A user can then instruct the apparatus to open the drawer, to remove the test device, ending the measurement procedure.

Assays and Analytes to be Detected

The system comprised of an apparatus and a test device as described herein is intended for detection of any analyte of interest. Analytes associated with a disorder or a contamination are contemplated, including biological and environmental analytes. Analytes include, but are not limited to, proteins, haptens, immunoglobulins, enzymes, hormones, polynucleotides, steroids, lipoproteins, drugs, bacterial antigens, viral antigens. With regard to bacterial and viral antigens, more generally referred to in the art as infections antigens, analytes of interest include *Streptococcus*, Influenza A, Influenza B, respiratory syncytial virus (RSV), hepatitis A, B and/or C, pneumoccal, human metapneumovirus, and other infectious agents well known to those in the art.

In some embodiments, a test device intended for detection of one or more of antigen associated with Lyme disease. In some embodiments, a test device designed for interaction with the apparatus is intended for use in the field of women's health. For example, test devices for detection of one or more of fetal-fibronectin, chlamydia, human chorionic gonadotropin (hCG), hyperglycosylated chorionic gonadotropin, human papillomavirus (HPV), and the like, are contemplated. In another embodiment, a test device for detection of vitamin D is designed for interaction with the apparatus and method of normalization described herein.

The test devices are intended for receiving a wide variety of samples, including biological samples from human bodily fluids, including but not limited to nasal secretions, nasopharyngeal secretions, saliva, mucous, urine, vaginal secretions, fecal samples, blood, etc.

The test devices, in some embodiments, are provided with a positive control swab or sample. In some embodiments, a negative control swab or sample is provided. For assays requiring an external positive and/or negative control, the apparatus is programmed to request a user to insert into the apparatus a test device to which a positive control sample or a negative control sample has been deposited. Kits provided with the test device can also include any reagents, tubes, pipettes, swabs for use in conjunction with the test device.

III. Examples

The following examples are illustrative in nature and are in no way intended to be limiting.

Example 1

Analysis of Test Device Utilizing a Normalization Target

Ten analyzers (instruments) were calibrated every day for 90 days, with a goal of reducing inter-analyzer and/or intra-analyzer variability by normalizing RFU values on a scan-by-scan basis using an embedded reference material (also known referred to as a "normalization target") mounted on the movable drawer of the instrument that receives a test device.

The results of two studies, "Study 1" and "Study 2" are presented below, in which the mean percent deviation in RFU with no normalization target and process, and mean percent range of RFU when including a normalization target and process for the ten analyzers is reported:

| Study 1 | | |
|---|---|---|
| | Deviation +/− | Normalized Range +/− |
| Mean of 10 instruments | 6.4% | 2.2% |

| Study 2 | | |
|---|---|---|
| | Deviation +/− | Normalized Range +/− |
| Mean of 10 instruments | 5.5% | 2.4% |

Without the use of a normalization target and procedure, the average intra-analyzer variability of the ten analyzers was 6.4%, whereas when the analyzers were normalized according to the methods described herein using normalization target that was scanned concurrent with each test device scan, the average variability was decreased to 2.2%. One particular instrument that had a 10% variability without a normalization target, improved by a factor of four with per-scan normalization.

Overall, using the system and methods disclosed herein for per-scan normalization, analyzer variability was reduced by a factor greater than about 2.

Example 2

Analysis of Test Device Utilizing a Normalization Target

Forty test devices for detection of human chorionic gonadotropin (hCG) were provided, and the same concentration of the same sample (20 mIU/mL) was placed on each device. The test devices were read in an instrument, by initiating an optical scan of the test device and a normalization target embedded in the optical path of the instrument. In each instance variability in the detected signal (RFU) was compared with and without per scan normalization, and a coefficient of variation (CV) determined.

| Per-scan normalization reduced the coefficient of variation (CV) by 1%. | | |
|---|---|---|
| | CV % | Normalized CV % |
| Reference Control (n = 40) | 13.64% | 12.58% |
| hCG Line (n = 6) | 12.30% | 9.56% |

In summary, per-scan normalization reduces analyzer variability, and false positives are prevented with a significantly improved CV.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method to improve precision of a test result from an optical instrument previously calibrated with an external calibrant and having stored in instrument memory a calibration value, comprising:
    providing the optical instrument comprising a normalization target embedded in or on the instrument, the normalization target having an assigned normalization value based on its detected signal relative to detected signal associated with the calibration value, the assigned normalization value stored in instrument memory;
    inserting an external calibrant into the instrument;
    collecting light emission data from the external calibrant and from the embedded normalization target in a single scan or image;
    assigning an updated normalization value to the embedded normalization target;
    scanning or imaging in a single scan:
        (i) a test cartridge inserted into the instrument to obtain a test signal; and
        (ii) the embedded normalization target to obtain a current normalization value; and
    optionally adjusting the test signal by a scaling factor based on the current normalization value, thereby obtaining a scaled test result with improved precision relative to test signal.

2. The method of claim 1, wherein, if the assigned normalization value exceeds a predefined value or differs from the current normalization value by more than about 2%, the instrument issues a communication to the user.

3. The method of claim 2, wherein the communication advises that an updated normalization value should be assigned to the embedded normalization target.

4. The method of claim 1, wherein the scaling factor used to adjust the test signal is a ratio of the current normalization value to the assigned normalization value.

5. The method of claim 1, wherein the embedded normalization target and the external calibrant are constructed from the same material.

6. The method of claim 1, wherein the embedded normalization target is affixed in an optical pathway in the instrument.

7. The method of claim 1, wherein the embedded normalization target is affixed to an element in the instrument that is capable of receiving a test strip.

8. The method of claim 1, wherein the optical instrument comprises an optics module for detecting at least one of emitted fluorescent light or emitted reflected light.

9. The method of claim 1, wherein the optical instrument comprises a digital camera to collect light output data from a test device and normalization target.

10. A method to improve precision of a test signal from an optical instrument previously calibrated with an external calibrant and having stored in instrument memory a calibration value, comprising:
    providing the optical instrument comprising a normalization target embedded in or on the instrument, the normalization target having an assigned normalization value based on its detected signal relative to detected signal associated with the calibration value, the assigned normalization value stored in instrument memory;
    scanning or imaging in a single scan:
        (i) a test cartridge inserted into the instrument to obtain a test signal; and
        (ii) the embedded normalization target to obtain a current normalization value; and
    optionally adjusting the test signal by a scaling factor based on the current normalization value, thereby obtaining a scaled test result with improved precision relative to test signal.

11. The method of claim 10, wherein if the normalization value exceeds a predefined value, a communication to a user is generated by the instrument.

12. The method of claim 11, wherein the communication advises that the instrument requires re-normalization with the embedded normalization target.

13. The method of claim 11, wherein the communication advises that an updated normalization value should be assigned to the embedded normalization target.

14. The method of claim 10, wherein collecting light emission data comprises optically interrogating with an excitation wavelength between about 300-800 nm.

15. The method of claim 10, wherein the instrument does not adjust the test signal by the scaling factor.

16. The method of claim 10, wherein the embedded normalization target is affixed in an optical pathway in the instrument.

17. The method of claim 10, wherein the embedded normalization target is affixed to an element in the instrument that is capable of receiving a test strip.

18. The method of claim 10, wherein the optical instrument comprises an optics module for detecting at least one of emitted fluorescent light or emitted reflected light.

19. The method of claim 10, wherein the instrument comprises a digital camera to collect light output data from a test device and normalization target.

* * * * *